United States Patent [19]
Idel et al.

[11] 3,991,062
[45] Nov. 9, 1976

[54] POLYMERIZABLE α,β-MONOOLEFINICALLY UNSATURATED MONOMERS CARRYING 8-HYDROXYQUINOYL GROUPS

[75] Inventors: Karsten Idel, Krefeld; Dieter Margotte, Krefeld-Bockum; Günther Reiff, Rua Poul Harris; Dieter Freitag, Krefeld-Traar; Hugo Vernaleken, Krefeld-Bockum, all of Germany

[73] Assignee: Bayer Aktiengesellschaft, Germany

[22] Filed: May 2, 1975

[21] Appl. No.: 573,838

Related U.S. Application Data
[63] Continuation-in-part of Ser. No. 549,275, Feb. 12, 1976, abandoned.

[30] Foreign Application Priority Data
Feb. 15, 1974 Germany.............................. 2407307
Feb. 15, 1974 Germany.............................. 2407306

[52] U.S. Cl.................. 260/287 XA; 260/23 AR; 260/32.6 NA; 260/41.52; 260/287 CE; 260/240 J
[51] Int. Cl.²........................................ C07D 215/14
[58] Field of Search................. 260/287 CE, 260 J

[56] References Cited
UNITED STATES PATENTS
3,299,044  1/1967  Cusic et al.................... 260/287 CE

OTHER PUBLICATIONS
Houben–Weyl "Methoden der Organischen Chemie" (1952) vol. 8, pp. 545–549, 655–658.

*Primary Examiner*—Nicholas S. Rizzo
*Assistant Examiner*—David E. Wheeler
*Attorney, Agent, or Firm*—Connolly and Hutz

[57] ABSTRACT

Polymerizable monomers of the formula I

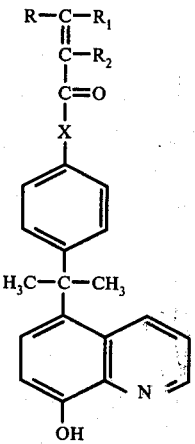

wherein
X denotes —O— or —NH—,
R denotes H—, —COOH or —COOR$_3$,
R$_1$ denotes —H or —CH$_3$ and
R$_2$ denotes H— or —CH$_3$, said monomers are obtained by acylation of 2-[4-hydroxyphenyl]-2-[5-(8-hydroxyquinolyl)]-propane or 2-[4-aminophenyl]-2-[5-(8-hydroxyquinolyl)]-propane with acid halides of the formula.

9 Claims, No Drawings

POLYMERIZABLE α,β-MONOOLEFINICALLY UNSATURATED MONOMERS CARRYING 8-HYDROXYQUINOYL GROUPS

This application is a continuation-in-part application of copending application Ser. No. 549,275, filed Feb. 12, 1975 now abandoned.

The invention relates to polymerisable α,β-monoolefinically unsaturated monomers carrying 8-hydroxyquinolyl groups, and to a process for their preparation.

It is known to react phenols or aromatic amines with carboxylic acid halides or carboxylic acid anhydrides under the conditions of a Schotten-Baumann reaction, or by the Einhorn method, to give the corresponding acylation products (compare Houben-Weyl, Methoden der Organischen Chemie (Methods of Organic Chemistry), (1952), volume 8, pages 545–549 and pages 655–658) and such acylation methods from Hebasis of the process for preparing the compounds according to the invention.

According to the present invention there are provided polymerisable monomers of the formula I

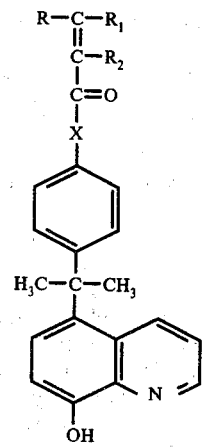

wherein
X denotes —O— or —NH—,
R denotes H—, —COOH or —COOR$_3$,
R$_1$ denotes —H or —CH$_3$ and
R$_2$ denotes H— or —CH$_3$.
Preferably, in the formula I,
R denotes H— or —COOC$_2$H$_5$, and
R$_1$ denotes H—.

The following may be mentioned specifically as examples of monomers of the formula I: 2-[4-methacryloyloxyphenyl]-2-[5-(8-hydroxyquinolyl)]-propane, 2-[4-acryloyloxyphenyl]-2-[5-(8-hydroxyquinolyl)]-propane, 2-[4-methacrylamidophenyl]-2-[5-(8-hydroxyquinolyl)]-propane, 2-[4-acrylamidophenyl]-2-[5-(8-hydroxyquinolyl)]-propane and 2-[4-(β-ethoxycarbonylacryloyloxyphenyl)]-2-[5-(8-hydroxyquinolyl)]-propane.

The invention also relates to a process for the preparation of the monomers according to formula I.

According to the invention there is provided a process for the preparation of monomers of the formula I comprising acylation 2-[4-hydroxy-phenyl]-2-[5-(8-hydroxyquinolyl)]-propane or 2-[4-aminophenyl]-2-[5-(8-hydroxyquinolyl)]-propane with acid halides of the formula

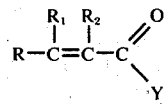

wherein
R denotes H, -COOH or COOR$_3$
R$_1$ denotes —H or —CH$_3$,
R$_2$ denotes —H or —CH$_3$, and
Y denotes —Cl or —Br
or with acrylic anhydride, methacrylic anhydride crotonic anhydride or maleic anhydride.

The compounds which serve as the starting material, namely 2-[4-hydroxyphenyl]-2-[5-(8-hydroxyquinolyl)]-propane and 2-[4-aminophenyl]-2-[5-(8-hydroxyquinolyl)]-propane do not form a subject of the present invention. They can be obtained by reaction of p-isopropenylphenol or p-isopropenylaniline with 8-hydroxyquinoline in the presence of suitable catalysts, in solution or in bulk, as can be seen in detail from the examples.

The acylation of the abovementioned amine or phenol can be carried out at temperatures of 0° to 100° C in bulk, in solution or by interphase reaction. Preferably, the acylation is carried out in an inert solvent such as methylene chloride, dichloroethane, chloroform, monochlorobenzene, dichlorobenzene, benzene, toluene or nitromethane.

If carboxylic acid halides, such as carboxylic acid chlorides or carboxylic acid bromides, preferably carboxylic acid chlorides, are employed, it is advisable to carry out the reaction in the presence of a hydrogen halide acceptor. This can be an alkali metal hydroxide, an alkali metal carbonate, an alkali metal acetate, a tert. amine such as pyridine, quinoline, isoquinoline, triethylamine or diethylaniline, or their mixtures. The hydrogen halide acceptor can be employed in an equivalent amount or in 1–50 times the equivalent amount, based on carboxylic acid halides.

Where carboxylic acid anhydrides are used, the acylation can be carried out in bulk or in the abovementioned solvents, under the same temperature conditions. Here, hydrogen halide acceptors are not necessary though it is frequently advantageous to carry out the acylation in the presence of small amounts (up to about 10% by weight, based on anhydride) of a tert. amine such as pyridine, concentrated sulphuric acid, zinc chloride or alkali metal acetates.

It is surprising, when carrying out the process according to the invention, that the 8-hydroxyl group in the quinoline does not undergo the acylation reaction.

Where the acylation is carried out in bulk with carboxylic acid anhydrides, the monomers according to the invention are obtained directly and can, if desired, be recrystallised from alcohols or aromatic hydrocarbons, such as benzene, and aliphatic hydrocarbons, such as petroleum ether. If the acylation is carried out in solvents with carboxylic acid halides or carboxylic acid anhydrides, the organic phase can be isolated, washed with acidified water and then with water, and concentrated.

It is also possible first to concentrate the organic phase, dilute it with fresh solvent, then wash it with acidified water and thereafter with water until neutral, and remove the organic solvent by distillation.

The polymerisable monomers according to the invention are valuable starting products for homopolymers and copolymers having a complex-forming action.

The term copolymer comprises not only copolymers with a statistical distribution of the copolymerised monomers and block copolymers, but also graft copolymers, where monomers are grafted onto a previously formed homopolymer or copolymer. Statistical copolymers are preferred.

As comonomers, one or more monomers from the following groups can be employed for the copolymerisation with at least one monomer of the formula I:

a. $\alpha,\beta$-Monoolefines with 2–4 C atoms, such as ethylene, propylene, butene-1 and isobutylene.

b. Conjugated diolefines with 4–6 C atoms, such as butadiene, isoprene, 2,3-dimethylbutadiene and 2-chlorobutadiene.

c. Acrylic acid and methacrylic acid, acrylonitrile and methacrylonitrile, acrylamide and methacrylamide, acrylic acid alkyl esters and methacrylic acid alkyl esters with 1–18, preferably 1–8, C atoms in the alcohol component, such as methyl acrylate, ethyl acrylate, propyl acrylate, isopropyl acrylate, n-butyl acrylate, 2-ethylhexyl acrylate, stearyl acrylate and the corresponding methacrylic acid alkyl esters.

d. Vinyl esters of organic monocarboxylic acids wherein the acid component contains 1–18, preferably 2–4 C atoms, such as vinyl acetate and vinyl propionate.

e. Monoolefinically unsaturated halogenohydrocarbons, preferably vinyl chloride or vinylidene chloride.

f. Vinylaromatics such as styrene, o- or p-methylstyrene, $\alpha$-methylstyrene, $\alpha$-methyl-p-isopropylstyrene, $\alpha$-methyl-m-isopropylstyrene or p-chlorostyrene, but preferably styrene.

In this category, the monomers which polymerise less readily, such as $\alpha$-methylstyrene and m- and p-isopropyl-$\alpha$-methylstyrene are preferably always employed as a mixture with at least one other of the copolymerisable monomers mentioned.

g. Monoesters of $\alpha,\beta$-monoolefinically unsaturated monocarboxylic acids, with 3–4 C atoms, and dihydric saturated aliphatic alcohols with 2–4 C atoms, such as 2-hydroxyethyl methacrylate, 2-hydroxypropyl methacrylate, 4-hydroxybutyl methacrylate, 2-hydroxyethyl acrylate, 2-hydroxypropyl acrylate and 4-hydroxybutyl acrylate.

h. N-Methylol ethers of acrylamide and methacrylamide, of the general formula II

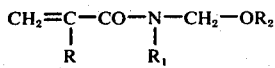

II in which

R represents hydrogen or methyl, $R_1$ represents hydrogen, alkyl, aralkyl or aryl, and $R_2$ represents alkyl or cycloalkyl, such as methyl, ethyl, n-propyl, isopropyl, n-butyl, isobutyl or cyclohexyl (compare German Auslegeschrift (German Published Specification) 1,035,363).

The N-methylol methyl ether of methacrylamide is preferred. The monomers of group (h) are employed, and incorporated into the copolymer, in amounts of 1–20% by weight, based on the total monomers.

i. Diesters and monoesters of maleic acid, fumaric acid and itaconic acid with 1–18 C atoms in the alcohol component, and also maleic anhydride, maleic acid or fumaric acid, amides of maleic acid and fumaric acid, maleimides and unsaturated copolymerisable polyesters which contain the radicals of maleic acid and/or fumaric acid as polymerisable constituents.

j. Vinyl alkyl ethers with 1–4 C atoms in the alkyl group, such as vinyl methyl ether, vinyl ethyl ether, vinyl propyl ether and vinyl butyl ether.

k. Monomers which have a crosslinking action and contain several non-conjugated olefinically unsaturated carbon-carbon bonds, such as divinylbenzene, diallyl phthalate, divinyl adipate, acrylic acid allyl ester and/or methacrylic acid allyl ester, methylene-bis-acrylamide, methylene-bis-methacrylamide, triallyl cyanurate, triallyl isocyanurate, triacryloyl-perhydro-S-triazine, bis-acrylates and bis-methacrylates of glycols or polyglycols with 2–20 C atoms, such as ethylene glycol diacrylate or dimethacrylate, propylene glycol diacrylate or dimethacrylate, butylene glycol 1,4-diacrylate or 1,4-dimethacrylate, tetraethylene glycol diacrylate or dimethacrylate and tris-acrylates and tris-methacrylates of trimethylolpropane and glycerol.

The crosslinking monomers of group (k) are preferably employed for the copolymerisation in amounts of 0.1–12% by weight, based on total monomers. They are incorporated into the copolymer in the same amounts.

In addition, primary, secondary or tertiary aminoalkyl esters of acrylic acid or methacrylic acid with, preferably, 2–4 C atoms in the alkyl group, and glycidol acrylate or methacrylate, can also be employed as co-monomers and can, if desired, be crosslinked, during or after the copolymerisation, via the amino or epoxide group, respectively.

Preferably, comonomers of groups (c) and (f) in combination with comonomers of group (k) are employed for the copolymerisation.

The comonomers can - unless stated otherwise - be employed for the copolymerisation in amounts of 5 to 95% by weight, preferably 50 to 90% by weight, based on total monomers. Correspondingly, the monomers of the formula I account for 5 – 95% by weight, preferably 50 to 10% by weight. They are also preferentially incorporated into the copolymers in these proportions. If, in addition to the customary comonomers, comonomers of groups (h) and (k), or yet other monomers copolymerisable with the monomers of the formula I, are also employed, their proportion shown under (h) and (k) is contained in the total proportion of the comonomers (5–95% by weight).

The homopolymers and copolymers can be prepared by radical or ionic chain mechanisms, in continuous or discontinuous processes.

In the case of the ionic polymerisation, catalysts of the anionic reaction type are preferably employed, in amounts of 0.01–5% by weight, preferably 0.01–2% by weight, based on total monomers; examples are metal alkyls, alkali metal alcoholates, metal amides or metal hydroxides, such as butyllithium, zinc alkyl with 1 – 4 C atoms in the alkyl groups, lithium alcoholate, potassium tert.-butylate, sodium amide or mixed catalysts, such as aluminium triethyl/titanium-IV chloride, used in aprotic solvents, such as, for example, dimethylformamide, dimethylaniline, benzene or toluene, at temperatures of about −80° C to approx. +110° C, preferably at −60° C to +10° C, if appropriate under pressure.

Preferably, the polymerisation takes place in accordance with the radical chain mechanism, in the presence of substances which yield free radicals.

Suitable substances of this type are inorganic per-compounds, such as potassium persulphate or ammonium persulphate, hydrogen peroxide, alkali percarbonates, organic peroxide compounds, such as acyl perodixes, for example dibenzoyl peroxide, dichlorobenzoyl peroxide, di-tert.-butyl peroxide and dicumyl peroxide, alkyl hydroperoxides, such as tert. butyl hydroperoxide, cumyl hydroperoxide and p-menthane hydroperoxide, organic percarbonates such as cyclohexyl peroxydicarbonate, diisopropyl peroxydicarbonate and ethylhexyl peroxydicarbonate, and also tert.-butyl peroctoate, tert.-butyl perpivalate and azodiisobutyronitrile. It is also possible to employ inorganic or organic per-compounds in combination with reducing agents, in a manner which is in itself known. Examples of suitable reducing agents are sodium pyrosulphite or sodium bisulphite, sulphinates, iron-II salts, cobalt naphthenate, ascorbic acid and aromatic amines such as p-toluidine.

Metal complexes, such as acetylacetonates of manganese and cobalt, and diacyl peroxide/tert. amine systems, are also suitable. However, the polymerisation can also be initiated by elevated temperatures, light rays and high energy rays.

Preferably, the copolymerisation is carried out with radical-forming substances such as azodiisobutyronitrile, benzoyl peroxide or potassium persulphate/sodium sulphite.

The amount of catalyst which can be used lies within the limits usually involved, that is to say approximately between 0.01 and 5% by weight, preferably between 0.01 and 2% by weight, calculated relative to the total monomers employed.

The polymerisation can be carried out at temperatures of −20° to 160° C, preferably at 60° to 110° C, if appropriate under pressure, in accordance with the customary methods of bulk polymerisation, solution polymerisation, precipitation polymerisation, dispersion polymerisation, emulsion polymerisation or bead polymerisation. Dispersion polymerisation and bead polymerisation, which — after separation from the dispersing medium — give the polymers in a form where they are immediately ready to use, are preferred. Solution polymerisation is particularly preferred.

If polymerisation is carried out in solution, the customary solvents are employed. Alcohols, such as ethanol to n-butanol, iso-butanol and tert.-butanol halogenated hydrocarbons such as methylene chloride, trichloroethylene and tetrachloroethane, ketones such as acetone and methyl ethyl ketone, esters such as ethyl acetate to octyl acetate, ethylglycol acetate and methylglycol acetate, ethylene glycol mono-methyl or bis-methyl ether, diethylene glycol monomethyl or bis-methyl ether and aromatic hydrocarbons such as toluene, benzene, xylene, dichlorobenzene and trichlorobenzene. The high polymers can be isolated either by steamstripping or by precipitation in a non-solvent such as petroleum, benzines, petroleum ether or methanol. They can also be isolated on screw evaporators. Further, the solutions can be isolated by spray-drying or drying in a thin layer evaporator, tube evaporator or falling film evaporator.

The precipitation polymerisation is preferably carried out in a good solvent for the monomer in which, however, the polymer is insoluble, such as, for example, in methanol or fluorochlorohydrocarbons, such as dichlorofluoromethane.

The dispersion polymerisation or bead polymerisation is carried out in an aqueous liquor in the presence of the customary protective colloids such as methylcellulose, gelatine, saponified polyvinyl acetate, styrene-maleic anhydride polymers, precipitated calcium phosphate or aluminium hydroxy gels. In addition, buffer substances such as sodium carbonate, prim-, sec- or tert-sodium phosphate and alkali metal borates can be added. In order to control the particle diameter, extraneous salts such as sodium sulphate, or alcohols such as butanol, can be present in amounts of 0.1 to 2% by weight, based on monomers.

The particle diameter can also be regulated by co-use of surface-active substances, such as fatty alcohol sulphonates or polyethylene oxides in which phenols were used as the starter (reaction products of phenols with ethylene oxide) and the like.

It is important to adjust the average molecular weight, and this can be done with the aid of 0.1 to 2% by weight, relative to total monomers, of a chain transfer agent. These agents are mercaptans, such as tert.-dodecylmetcaptan, xanthates, thioglycerol, nitrotoluenes, cumene, halogen derivatives such as carbon tetrachloride, haloforms such as chloroform, methyl vinyl carbinol, allyl alcohol and the like. The regulators are employed in such amounts that average molecular weights of 5,000 to 500,000 result. After the dispersion polymerisation or bead polymerisation the particles of diameter 10 $\mu$ to 2 mm are separated from the aqueous liquor and washed and dried. Thereafter they are, in most cases, in a free-flowing form.

These polymers containing 8-hydroxyquinoline groups can be employed, in the solid form or dissolved in organic solvents for removing from solutions metal ions of the transition elements of the periodic table of the elements, that is to say of the elements Sc to Zn (atomic numbers 21 to 30), Y to Cd (atomic numbers 39–48), La to Hg (atomic numbers 57–80) and Ac to U (atomic numbers 89–92), and of magnesium, calcium, aluminium, lead and bismuth. The metal ions can again be separated off by elution with strong acids or bases or stronger complex-forming agents such as, for example, nitrilotriacetic acid. The polymers described are therefore of particular interest for the removal of traces of heavy metals from industrial effluents or process sewage.

The polymers prepared with the monomers according to the invention can also be employed for the complexing of interfering metallic impurities in thermoplastics or thermosetting resins, in amounts of 0.01 to 10% by weight based on the total mixture. Thus, as is known, iron impurities in polyvinyl chloride lower the heat stability but the latter can be improved by complexing the iron with the polymers described.

By controlled reaction of the polymers carrying 8-hydroxyquinoline, or of the monomers according to the invention, with suitable metal compounds, polymers or monomers containing metal are obtained which can be used as catalysts, especially for reactions which take place by a radical mechanism.

The monomers can also be added directly as stabilisers to polymers containing chlorine such as PVC, polyvinylidene chloride or chlorinated rubber.

The polymers themselves are not a subject of the present invention.

The percentages in the examples are by weight, unless noted otherwise.

PREPARATION OF THE STARTING MATERIAL, 2-[4-HYDROXYPHENYL]-2-[5-(8-HYDROXYQUINOLYL)]-PROPANE.

1,508 g of 8-hydroxyquinoline, 483 g of p-isopropenylphenol and 150 g of bentonite (acid catalyst K 20 from Messrs. Sudchemie, Munich) are brought together and heated to 180° C for 24 hours in a nitrogen atmosphere under reflux. The reaction miture is then filtered through a pressure filter to separate off the solid catalyst.

After addition of methylene chloride/water, a part of the 2-[4-hydroxyphenyl]-2-[5-(8-hydroxyquinolyl)]-propane is obtained in a crystalline form. The mixture which remains is subjected to a steam distillation, whereby the 8-hydroxyquinoline employed in excess can be recovered. on renewed addition of methylene chloride, a further part of the functional hydroxyquinoline is obtained in a crystalline form.

The two crystalline fractions, when combined, give a total yield of 460 g (46% of theory). After extraction with benzene in a Soxhlet, colourless crystals of melting point 139° C are obtained from benzene.

| Analysis:  | C     | H     | N     |
|------------|-------|-------|-------|
| calculated | 77.4% | 6.10% | 5.01% |
| found      | 77.5% | 6.03% | 4.87% |

EXAMPLE 1:

2-[4-Methacryloyloxyphenyl]-2-[5-(8-hydroxyquinolyl]-propane 279 g of 2-[4-hydroxyphenyl]-2-[5-(8-hydroxyquinolyl)]-propane are introduced into 1,120 ml of methylene chloride and a solution of 190.8 g of sodium carbonate in 1,000 ml of water together with 3.0 ml of triethylamine is added dropwise at 13° C. 110 g of methacrylic acid chloride and 200 ml of methylene chloride are then added over the course of 20 minutes.

The mixture is stirred for a further 20 minutes and the organic phase is separated off and washed once with dilute HCl and then with water until neutral. After concentrating the organic phse in vacuo, 180 g (52% of theory) of the methacrylic acid ester of 2-(4-methacryloyloxyphenyl)-2-[5-(8-hydroxyquinolyl)]-propane are obtained from ethanol as colourless crystals of melting point 141° C.

| Analysis:  | C      | H     | N     |
|------------|--------|-------|-------|
| calculated | 76.06% | 6.09% | 4.03% |
| found      | 75.6%  | 6.05% | 3.94% |

PREPARATION OF THE STARTING MATERIAL: 2-[4-AMINOPHENYL]-2-[5-(8-HYDROXYQUINOLYL)]-PROPANE 2,180 g of 8-hydroxyquinoline, 400 g of p-isopropenylaniline and 300 g of bentonite (acid catalyst K 20 from Messrs. Sudchemie, Munich) are heated for 26 hours to 160° C under reflux in a nitrogen atmosphere. The reaction mixture is filtered through a pressure filter and then successively subjected first to a vacuum distillation and then to a steam distillation. This results in almost quantitative recovery of the 8-hydroxyquinoline employed in excess. Methylene chloride is then added to the reaction mixture and the organic phase is separated off. The residue remaining after concentrating the organic phase is extracted with a methylene chloride/petroleum ether mixture and 382 g (46% of theory) of 2-(4-aminophenyl)-2-[5-(8-hydroxyquinolyl)]-propane of melting point 105°–107° C are obtained. Crystallisation from ethanol raises the melting point of the colourless crystals to 109° C.

| Analysis:  | C     | H     | N      |
|------------|-------|-------|--------|
| calculated | 77.7% | 6.46% | 10.02% |
| found      | 77.5% | 6.58% | 9.88%  |

EXAMPLE 2:

2-[4-Methacrylamidophenyl]-2-[5-(8-hydroxyquinolyl)]-propane 200 g of 2-(4-aminophenyl)-2-[5-(8-hydroxyquinolyl)]-propane are dissolved in 200 ml of methylene chloride and 500 ml of pyridine. 75.0 g of methacrylic acid chloride in 1,000 ml of methylene chloride are slowly added dropwise to this solution. The mixture is left to stand for 15 hours at room temperature and the solvents are then removed in vacuo. The residue is taken up in methylene chloride and washed twice with 1 N $H_2SO_4$ and then with water. After concentrating the organic phase, 205 g (80.5% of theory) of 2-(4-methacrylamidophenyl)-2-[5-(8-hydroxyquinolyl)]-propane are obtained in the form of colourless crystals of melting point 126°–127° C from benzene/petroleum ether.

| Analysis:  | C     | H     | N     |
|------------|-------|-------|-------|
| calculated | 76.5% | 6.30% | 8.11% |
| found      | 76.3% | 6.18% | 8.02% |

Use of the monomers according to the invention

A. To a 50 per cent strength solution of 20 g of 2-[4-methacryloyloxyphenyl]-2-[5-(8-hydroxyquinolyl)]-propane and 80 g of methyl methacrylate in toluene and 2% by weight of tert. dodecylmercaptan, relative to the monomer, are added dropwise 2% by weight of dibenzoyl peroxide, relative to the monomers, in toluene, at 100° C over the course of 3 to 4 hours. Thereafter the mixture is stirred for a further 4 hours at 100° C. The vinyl polymer is then either precipitated in methanol or poured out onto a metal sheet and dried in a vacuum drying cabinet. The average molecular weight of the statistical copolymer was determined osmometrically. $M_n = 37,000$, nitrogen analysis: calculated 0.8%, found 0.78%.

3 g of the polymer are dissolved in 150 ml of methylene chloride and shaken with 180 ml of an 0.1% strength by weight solution of mercury-II acetate for 3 hours. The phases are then separated and the mercury content of the aqueous phase is determined. Residual content of Hg: 0.7 mg/l $\triangleq$ 0.7 ppm of Hg.

4 g of the polymer are dissolved in 200 ml of methylene chloride and shaken with 0.42 g of copper-II acetate for 4 hours. The reaction solution is filtered and the residue remaining after removing the solvent is analysed. Copper content of the polymer: 2.9%.

B. 90 g of styrene and 10.0 g of 2-[4-methacrylamido)phenyl]-2-[5-(8-hydroxyquinolyl)]-propane are dissolved in toluene together with 2% by weight of tert. dodecylmercaptan, relative to the monomers, and the solution is heated to 100° C. 2 g of dibenzoyl peroxide in toluene are added dropwise over the course of 2 to 3 hours to this reaction mixture and the reaction is allowed to continue for a further 6 hours.

Thereafter, the product is either precipitated in an alcohol or dried after removal of the solvent in a vacuum drying cabinet. The average molecular weight was determined osmometrically. Mn = 26,200. Nitrogen analysis: calculated: 0.81; found: 0.80%.

4 g of the polymer are dissolved in 200 ml of methylene chloride and shaken with 210 mg of copper-II acetate for 2 hours. The reaction solution is filtered and the solvent is removed. The residue which remains was examined for its copper content. Copper content: 2.7% by weight.

We claim:
1. A compound of the formula

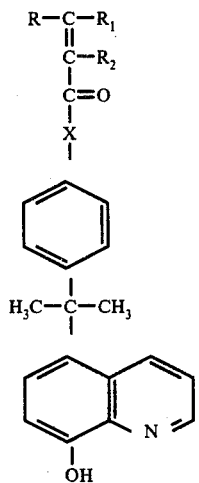

wherein X is O or NH; R is H, COOH or $COOR_3$ wherein $R_3$ is $C_1$–$C_{18}$ alkyl or cyclohexyl; $R_1$ is H or $CH_3$ and $R_2$ is H or $CH_3$.

2. The polymerisable compound of claim 1 wherein $R_3$ is $C_1$–$C_8$ alkyl or cyclohexyl.

3. The polymerisable compound of claim 1 wherein R is H or $COOC_2H_5$ and $R_1$ is H.

4. 2-[4-Methacryloyloxyphenyl]-2-[5-(8-hydroxyquinolyl]-propane.

5. 2-[4-Methacrylamidophenyl]-2-[5-(8-hydroxyquinolyl]-propane.

6. 2-[4-($\beta$-Ethoxycarbonylacryloyloxyphenyl)]-2-[5-(8-hydroxyquinolyl)]-propane.

7. A process for preparing a compound of claim 1 which comprises the step of acylating 2-[4-hydroxyphenyl]-2-[5-(8-hydroxyquinolyl)]propane or 2-[4-aminophenyl]-2-[5-(8-hydroxyquinolyl)]-propane with (1) an acid halide of the formula

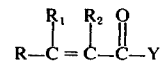

wherein R is H, COOH or $COOR_3$; $R_3$ is $C_1$–$C_{18}$ alkyl or cyclohexyl, $R_1$ is H or $CH_3$, $R_2$ is H or $CH_3$ and Y is Cl or Br or with (2) acrylic anhydride, methacrylic anhydride, crotonic anhydride or maleic anhydride.

8. The process of claim 7 wherein $R_3$ is $C_1$–$C_{18}$ alkyl or cyclohexyl.

9. The process of claim 7 wherein R is H or $COOC_2H_5$ and $R_1$ is H.

* * * * *